(12) United States Patent
Irikura et al.

(10) Patent No.: US 7,279,543 B2
(45) Date of Patent: Oct. 9, 2007

(54) ANTI-BACTERIAL POLYMER AND METHOD FOR THE PREPARATION THEREOF, ANTI-BACTERIAL POLYMER FILM AND METHOD FOR THE PREPARATION THEREOF, AND ARTICLE HAVING SUCH A FILM ON THE SURFACE THEREOF

(75) Inventors: Hagane Irikura, Ibaraki-ken (JP); Yoshikazu Takahashi, Ibaraki-ken (JP)

(73) Assignee: Ulvac, Inc., Kanagawa (JP)

( * ) Notice: Subject to any disclaimer, the term of this patent is extended or adjusted under 35 U.S.C. 154(b) by 339 days.

(21) Appl. No.: 10/655,568

(22) Filed: Sep. 5, 2003

(65) Prior Publication Data
US 2004/0077819 A1   Apr. 22, 2004

(30) Foreign Application Priority Data
Sep. 6, 2002 (JP) .............................. 2002-261424
Aug. 12, 2003 (JP) .............................. 2003-292039

(51) Int. Cl.
*C08G 18/10* (2006.01)
*C08G 18/28* (2006.01)
*C08G 12/02* (2006.01)
*C08G 69/08* (2006.01)
*C08G 69/00* (2006.01)

(52) U.S. Cl. ........................... 528/60; 528/61; 528/64; 528/266; 528/310; 528/335; 528/331; 528/350; 528/353

(58) Field of Classification Search ................ 528/170, 528/310, 322, 353, 60, 61, 64, 266, 331, 528/350, 335
See application file for complete search history.

(56) References Cited

U.S. PATENT DOCUMENTS

| 2,393,673 | A | | 1/1946 | Wyss et al. |
| 4,180,614 | A | | 12/1979 | Angelo et al. |
| 4,624,867 | A | * | 11/1986 | Iijima et al. ............. 427/255.6 |
| 4,746,566 | A | * | 5/1988 | Connolly ..................... 442/59 |
| 4,759,958 | A | * | 7/1988 | Numata et al. ........... 427/255.6 |
| 4,999,215 | A | * | 3/1991 | Akagi et al. ................ 427/488 |
| 6,379,743 | B1 | | 4/2002 | Lee et al. |
| 2004/0077819 | A1 | * | 4/2004 | Irikura et al. ................ 528/44 |

FOREIGN PATENT DOCUMENTS

| JP | 03050709 | | 3/1991 |
| JP | 07258370 | | 10/1995 |
| JP | 09-216999 | | 8/1997 |
| JP | 11106506 | | 4/1999 |
| JP | 11-236447 | | 8/1999 |
| JP | 2001-106911 | | 4/2001 |
| JP | 2003-292039 | * | 8/2003 |

* cited by examiner

*Primary Examiner*—Ana Woodward
(74) *Attorney, Agent, or Firm*—Arent Fox LLP

(57) ABSTRACT

An anti-bacterial polymer of the present invention consists of a vapor deposition-polymerization reaction product of a diaminobenzoic acid monomer or halogen atom-containing diamine monomer and a monomer reactive with these monomers. The anti-bacterial polymer can be prepared by a method, which comprises the step of subjecting a gas obtained by evaporating a diaminobenzoic acid monomer or halogen atom-containing diamine monomer and a gas obtained by evaporating a monomer reactive with these monomers to vapor deposition-polymerization, in a vacuum, to thus form an anti-bacterial polymer. The method permits the formation of a film having a desired thickness even on the surface having a complicated shape such as the surface of, for instance, a heat exchanger.

13 Claims, 1 Drawing Sheet

ANTI-BACTERIAL POLYMER AND METHOD FOR THE PREPARATION THEREOF, ANTI-BACTERIAL POLYMER FILM AND METHOD FOR THE PREPARATION THEREOF, AND ARTICLE HAVING SUCH A FILM ON THE SURFACE THEREOF

BACKGROUND OF THE INVENTION

The present invention relates to an anti-bacterial polymer and a method for the preparation of the same, an anti-bacterial polymer film and a method for the preparation thereof, and an article having, on the surface, such an anti-bacterial polymer film. Thus, the present invention permits the application of an anti-bacterial polymer film on the surface of an article such as members and products used in, for instance, housing or building materials and heat exchangers of air-conditioning systems.

As a method for the preparation of an anti-bacterial plastic, there has in general been known a technique in which an anti-bacterial agent is incorporated into a plastic material through melting with heating. This incorporation process requires the use of an anti-bacterial agent having such heat resistance that it can in general withstand the temperature ranging from 250 to 300° C. or higher, although the heat resistance required for the anti-bacterial agent may vary depending on the kinds of plastics used and the processing techniques selected. More specifically, such an anti-bacterial agent is used for preventing any weight change and discoloration of the anti-bacterial agent and any reduction of the anti-bacterial effect of the resulting plastic material because of the volatilization, decomposition of the anti-bacterial agent and the release of moisture contained therein. Examples of plastics used include polyethylene, polystyrene, poly(vinyl chloride) and polypropylene. The foregoing anti-bacterial plastic (product) is, for instance, prepared by the addition of a master batch or plastic pellets containing an anti-bacterial agent in a high concentration on the order of about 5 to 30% to a desired plastic material, mixing them and then molding the resulting mixture. The concentration of the anti-bacterial agent in the final product is mainly set at the range of from about 0.3 to 2%. As an example of the conventional technique for the foregoing incorporation, there has been known an anti-bacterial resin product obtained by adding an anti-bacterial agent consisting of soluble glass to a polycarbonate resin and then incorporating the former into the latter (see, for instance, Japanese Patent No. 3,271,888 (claim 1)).

In addition, there has also been known a method for preparing a polyurea resin for a resist or an electrical insulation material by evaporating, in a vacuum, (a) a specific diamine component such as 4,4'-diaminodiphenyl-methane and (b) a diisocyanate component from separate evaporation sources, forming a polyurea film on a substrate through vapor deposition-polymerization and then irradiating the polyurea film with ultraviolet rays and/or an electron beam (see, for instance, Japanese Un-Examined Patent Publication (hereunder referred to as "J.P. KOKAI") Hei 7-258370 (claim 1, pages 1-2)).

Moreover, there has also been known a polyimide resin, as a component for a polyimide resin composition, prepared through solution polymerization of a diamino-benzoic acid and pyromellitic acid anhydride (see, for instance, J.P. KOKAI 2001-106911 (claim 5, pages 10-11).

Furthermore, there has also been known a vapor deposition-polymerized film of polyimide prepared by the vapor deposition-polymerization of a specific acid anhydride such as 3,3',4,4'-bisphenyltetracarboxylic acid anhydride with a specific diamine such as 2,2-bis[4-(4-aminophenoxy)phenyl]propane (see, for instance, J.P. KOKAI Hei 11-236447 (claims 1 and 2)).

In all of the foregoing patent articles, it is not disclosed and/or suggested that an anti-bacterial polymer can be formed by the vapor deposition-polymerization of a diamino-benzoic acid and a monomer reactive with the benzoic acid.

In addition, in most cases, the anti-bacterial properties are imparted to an article such as a member or a product of a metal or a ceramic material by applying an anti-bacterial plastic film onto the surface of such an article using, for instance, an adhesive. For this reason, a problem arises such that it is quite difficult to apply an anti-bacterial agent to the entire surface of an article such as a member or a product having a complicated shape. Accordingly, there has been desired for the development of an anti-bacterial polymer capable of being applied onto the surface of an article having a complicated surface shape.

SUMMARY OF THE INVENTION

Accordingly, it is an object of the present invention to solve the foregoing problems associated with the conventional techniques and to develop an anti-bacterial vapor deposition-polymerization reaction product, which has never been prepared by the conventional technique. More specifically, it is an object of the present invention to provide an anti-bacterial polymer and a method for the preparation of the same. It is another object of the present invention to provide an anti-bacterial polymer film and a method for the preparation thereof. It is a still another object of the present invention to provide an article having, on the surface, the foregoing anti-bacterial polymer film.

The inventors of this invention have conducted various studies to solve the foregoing problems, have found that a polymer film prepared using a diaminobenzoic acid monomer among the polymer films prepared by the vapor deposition polymerization shows excellent anti-bacterial effect and have thus completed the present invention.

According to an aspect of the present invention, there is provided an anti-bacterial polymer comprising a vapor deposition-polymerization product of a diamino-benzoic acid monomer or halogen atom-containing diamine monomer and a monomer reactive with this benzoic acid monomer or halogen atom-containing diamine monomer.

In an embodiment of this anti-bacterial polymer, the diamino-benzoic acid monomer may be a member selected from 2,3-diaminobenzoic acid, 2,4-diaminobenzoic acid, 2,5-diaminobenzoic acid, 3,4-diaminobenzoic acid and 3,5-diaminobenzoic acid.

The halogen atom may be selected from the group consisting of fluorine, chlorine, bromine, and iodine.

The halogen atom-containing diamine monomer may be a monomer selected from 4,4'-methylenebis(2-chlorobenzene amine), 3,3'-dichloro-4,4'-diaminodiphenyl ether, and 5-chloro-m-phenylenediamine.

In another embodiment of the anti-bacterial polymer, the monomer reactive with this benzoic acid monomer or halogen atom-containing diamine monomer is a member selected from the group consisting of tetracarboxylic acid dianhydride, diisocyanate, acid chlorides and aldehyde.

The foregoing anti-bacterial polymer may be a polyimide, a polyamide, a polyurea or a poly(azomethine). The polyimide is a copolymer comprising at least one structural unit represented by the following general formula (I):

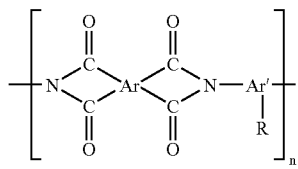

(in the formula (I), Ar and Ar' each represents an aromatic group selected from phenyl groups, tolyl groups and phenethyl groups or aliphatic group, and R is COOH or a halogen atom selected from fluorine, chlorine, bromine, and iodine). The foregoing polyamide is a copolymer comprising at least one structural unit represented by the following general formula (II):

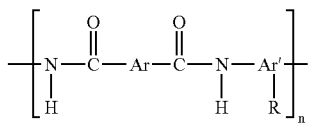

(in the formula (II), Ar and Ar' each represents an aromatic group selected from phenyl groups, tolyl groups and phenethyl groups or aliphatic group, and R is COOH or a halogen atom selected from fluorine, chlorine, bromine, and iodine). The foregoing polyurea is a copolymer comprising at least one structural unit represented by the following general formula (III):

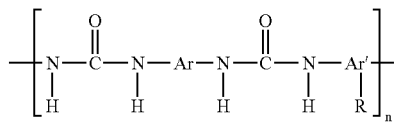

(in the formula (III), Ar and Ar' each represents an aromatic group selected from phenyl groups, tolyl groups and phenethyl groups or aliphatic group, and R is COOH or a halogen atom selected from fluorine, chlorine, bromine, and iodine). The foregoing poly(azomethine) is a copolymer comprising at least one structural unit represented by the following general formula (IV):

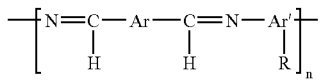

(in the formula (IV), Ar and Ar' each represents an aromatic group selected from phenyl groups, tolyl groups and phenethyl groups, or aliphatic group, and R is COOH or a halogen atom selected from fluorine, chlorine, bromine, and iodine).

The method for the preparation of the anti-bacterial polymer according to the present invention is characterized in that a gas obtained by evaporating a diaminobenzoic acid monomer or halogen atom-containing diamine monomer is subjected to vapor deposition polymerization, in a vacuum, with a gas obtained by evaporating a monomer reactive with the diaminobenzoic acid monomer or halogen atom-containing diamine monomer to thus form an anti-bacterial polymer.

The diaminobenzoic acid monomer, halogen atom-containing diamine monomer and the monomer reactive with the diaminobenzoic acid monomer or halogen atom-containing diamine monomer used in the foregoing preparation method as well as the resulting anti-bacterial polymer or the polyamide, polyimide, polyurea, or poly(azomethine) are the same as those specified above.

The anti-bacterial polymer film according to the present invention consists of the foregoing anti-bacterial polymer.

The method for preparing such an anti-bacterial polymer film is characterized by subjecting a gas obtained by evaporating a diaminobenzoic acid monomer or halogen atom-containing diamine monomer and a gas obtained by evaporating a monomer reactive with the diaminobenzoic acid monomer or halogen atom-containing diamine monomer to vapor deposition-polymerization on a substrate in a vacuum to thus form an anti-bacterial polymer film. The diaminobenzoic acid monomer, halogen atom-containing diamine monomer and the monomer reactive with the diaminobenzoic acid monomer or halogen atom-containing diamine monomer used herein as well as the resulting anti-bacterial polymer or the like are identical to those described above.

After the vapor deposition of the foregoing raw substances or the formation of a film on the substrate, it is preferred to optionally subject the resulting film to a heat treatment at a desired temperature when the vapor deposition-polymerization reaction insufficiently proceeds. This heat treatment may assist such an insufficient polymerization reaction and therefore, the resulting film would have improved heat resistance.

In addition, the article of the present invention is a member or a product having, on the surface thereof, an anti-bacterial polymer film comprising the foregoing antibacterial polymer.

DESCRIPTION OF THE PREFERRED EMBODIMENTS

Figure 1:
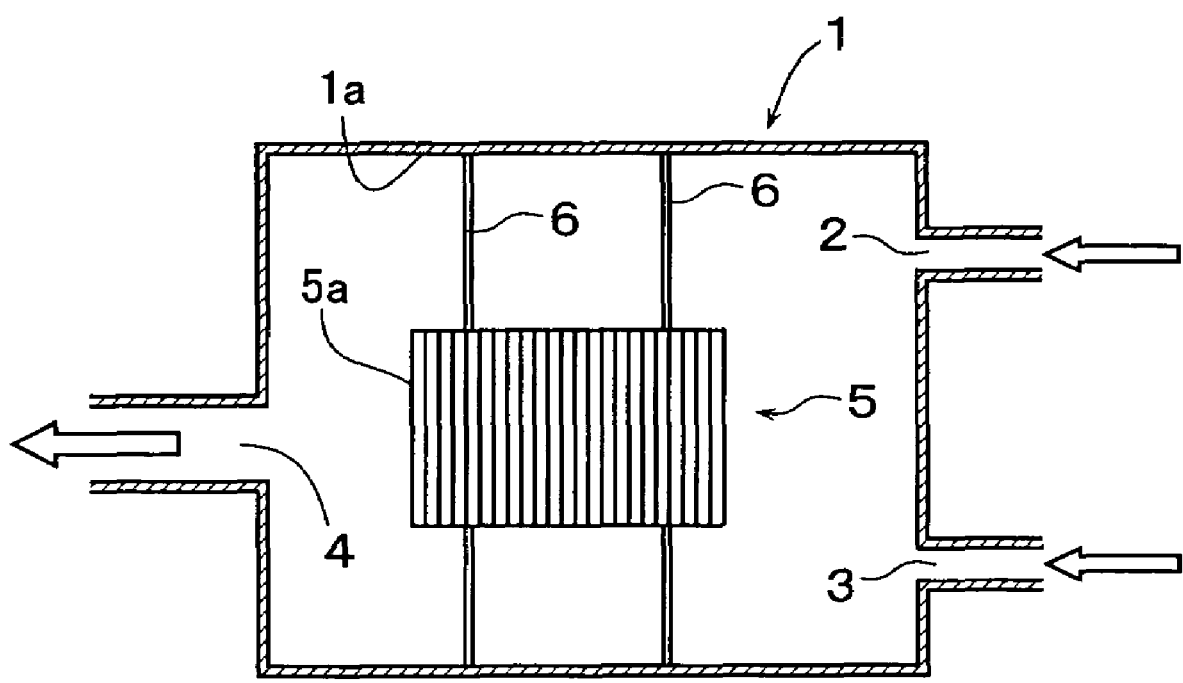
FIG. 1 is a schematic cross sectional view showing an embodiment of a vapor deposition-polymerization device used for the preparation of an anti-bacterial polymer film according to the present invention.

The anti-bacterial polymer and the method for the preparation of the same, the anti-bacterial polymer film and the method for the preparation thereof, and the article having, on the surface, the anti-bacterial polymer film according to the present invention will hereunder be described in more detail.

According to the present invention, a diaminobenzoic acid monomer or halogem atom-containing diamine monomer is reacted with a monomer reactive with the diaminobenzoic acid monomer or halogen atom-containing diamine monomer through a vapor deposition-polymerization reaction to thus form an anti-bacterial polymer.

The diaminobenzoic acid monomers may be those listed above and the halogen atom-containing diamine monomers may be compounds listed below in addition to those described above:

Examples of additional halogen atom-containing diamine monomers are halogen atom-containing aliphatic diamines such as N,N'-bis-chloroacetyl ethylene diamine, N-acetyl-N'-chloroacetyl ethylene diamine, N,N'-bis-(3-chloropropionyl)ethylene diamine, N-propionyl-N'-(α-bromo-isovaleryl)ethylene diamine, N,N'-bis-chloroacetyl trimethylene diamine, N,N'-bis-chloroacetyl tetramethylene diamine, N,N'-bis(2-bromo-propionyl)tetramethylene diamine, N-(2-bromoethyl)pentamethylene diamine, N-(3-bromopropyl) pentamethylene diamine, N,N'-bis-chloroacetyl pentamethylene diamine, N,N'-bis-(3-chloropropionyl)hexamethylene diamine and N,N'-bis-(11-bromo-undecanoyl)hexamethylene diamine; and halogen atom-containing aromatic diamines such as N-(o-chlorophenyl)-o-phenylene diamine, 4-chloro-o-phenylene diamine, 3,5-dichloro-o-phenylene diamine, 3,6-dichloro-o-phenylene diamine, 4-bromo-o-phenylene diamine, 3,5-dibromo-o-phenylene diamine, 3,6-dibromo-o-phenylene diamine, 4,5-dibromo-o-phenylene diamine, 3,4,5-tribromo-o-phenylene diamine, 4-chloro-m-phenylene diamine, 2,5-dichloro-m-phenylene diamine, 4,6-dichloro-m-phenylene diamine, 4-bromo-m-phenylene diamine, 5-bromo-m-phenylene diamine, 4,6-dibromo-m-phenylene diamine, 2,4,6-tribromo-m-phenylene diamine, 2,4,5,6-tetrabromo-m-phenylene diamine, 4,6-diiodo-m-phenylene diamine, N-4-chlorophenyl-p-phenylene diamine, N-4-bromophenl-p-phenylene diamine, 2,5-dichloro-p-phenylene diamine, 2,6-dichloro-p-phenylene diamine, 2,3,5,6-tetrachloro-p-phenylene diamine, 2,5-dibromo-p-phenylene diamine, 2,6-dibromo-p-phenylene diamine, 2,6-diiodo-p-phenylene diamine, 2-chloro-3,5-diaminotoluene, 2,4-dichloro-3,5-diaminotoluene, 2,6-dichloro-3,5-diaminotoluene, 5-chloro-2,4'-diaminodiphenyl, 5-bromo-2,4'-diamino-diphenyl, 2,2'-dichlorobenzidine, 3,3'-dichlorobenzidine, 2,2'-dibromobenzidine, 3,5,3',5'-tetrabromo-benzidine, 2,2'-dichloro-3,3'-dimethylbenzidine, 5,5'-dichloro-3,3'-dimethyl-benzidine, 2'',5''-dichloro-4,4'-diaminotriphenylmethane, 3-chloro-2,5-diaminohydroquinone, 3,6-dichloro-2,5-diaminohydroquinone, 2-chloro-4,6-diaminoresorcin, 2,2'-bis-(trifluoromethyl)benzidine and 2,2'-bis-(p-aminophenyl)-1,1,1,3,3,3-hexafluoropropane.

Specific examples of such monomers reactive with the diaminobenzoic acid monomer or halogen atom-containing diamine monomer include tetracarboxylic acid dianhydrides such as pyromellitic acid dianhydride, oxy-diphthalic acid dianhydride and biphenyl-3,4,3',4'-tetracarboxylic acid dianhydride; diisocyanates such as 4,4'-methylene-bis(phenyl isocyanate), hexamethylene diisocyanate and 3,3'-dimethyldiphenyl-4,4'-diisocyanate; acid chlorides such as terephthaloyl dichloride and isophthaloyl dichloride; and aldehydes such as terephthal aldehyde and isophthal aldehyde. Among these monomers, preferred are pyromellitic acid dianhydride, oxy-diphthalic acid dianhydride, 4,4'-methylene-bis(phenyl isocyanate), terephthaloyl dichloride and terephthal aldehyde.

When forming a film of the foregoing anti-bacterial polymer on the surface of an article to be treated through a vapor deposition-polymerization reaction, it is possible to use a vapor deposition-polymerization device such as that schematically depicted on FIG. 1. This vapor deposition-polymerization device 1 is provided with a pair of gas inlets or the first gas inlet 2 and the second gas inlet 3 for introducing monomer gases through corresponding gas-introduction valves, respectively at desired positions on the side wall of the device and a vacuum exhaust port 4 for the evacuation through an exhaust valve (not shown) communicated with an oil diffusion pump at a desired position on the side wall opposite to the foregoing paired inlets.

The gas-introduction valves are designed in such a manner that they can maintain a desired temperature by the action of a heating means.

An article 5 to be treated is arranged in the interior of the vapor deposition-polymerization device 1 by, for instance, suspending the article from the ceiling 1a of the device 1 through a cable 6, which can sufficiently withstand a desired tension. In this case, an appropriate means for supporting the article 5 to be treated such as a holder may be positioned within the device 1. In this connection, it is necessary to position the article 5 to be treated within the device 1 such that all of the faces thereof to be subjected to an anti-bacterial treatment are exposed or are not covered.

Moreover, the vapor deposition-polymerization device 1 is also provided with a temperature control means for the control of the internal temperature of the device 1 so that a desired quantity of heat can be supplied to the vapor deposition-polymerization reaction. For this reason, the whole surface of the article 5 to be treated is uniformly heated due to the radiant heat from the inner wall of the device 1, which is heated by the foregoing temperature control means. In this case, it is also possible to dispose a means for directly heating the article per se to be treated or the surface thereof.

Using the vapor deposition-polymerization device 1 having such a structure discussed above, the device 1 is first evacuated through the exhaust valve communicated with the vacuum exhaust port 4, while an article 5 to be treated is positioned within the device 1, to thus establish, within the device 1, a reduced pressure suitable for the vapor deposition-polymerization reaction, for instance, ranging from 10+1 to $10^{-5}$ Pa and preferably $10^{-2}$ to $10^{-3}$ Pa. Then the temperature in the device is adjusted to a level suitable for the vapor deposition-polymerization reaction, for instance, 200° C. by the temperature control means while maintaining the foregoing pressure and such conditions are maintained. At this stage, gaseous diaminobenzoic acid (such as 3,5-diaminobenzoic acid (DBA)) contained in a container heated to a desired temperature in advance is introduced into the device through the first gas inlet 2 and, simultaneously, a gaseous monomer (such as pyromellitic acid dianhydride (PMDA)) reactive with the gaseous diaminobenzoic acid contained in a container heated to a desired temperature in advance is introduced into the device through the second gas inlet 3. Then these conditions are maintained over a desired period of time (such as one hour) so that the vapor deposition-polymerization reaction proceeds to thus uniformly form an anti-bacterial polymer film having a desired thickness on the entire surface of the article 5.

The foregoing pressure and temperature within the device used in the foregoing vapor deposition-polymerization process may be established to desired levels, respectively by the simultaneous evacuation and heating operations.

Although the foregoing vapor deposition-polymerization device is designed in such a manner that the gaseous monomers are introduced into the device through the corresponding gas-introduction valves from the external sources, the device may likewise be designed such that the device is equipped with evaporation sources for the monomers and that the vapor deposition-polymerization reaction is carried out under the same conditions therein using the gaseous monomers generated from these evaporation sources.

The foregoing article to be processed is not restricted to any specific one and the anti-bacterial polymer film according to the present invention can be applied to a wide variety of products, which are touched with the hands of many and unspecified persons and used by such persons, for instance, metallic products such as doorknobs, metallic products used in hospitals and metallic products for aircrafts.

The present invention will hereunder be described in more detail with reference to the following Examples, but the present invention is not restricted to these specific Examples at all.

EXAMPLE 1

An anti-bacterial polymer film was applied onto the surface of a heat exchanger 5 for an air conditioner as an article to be treated through a vapor deposition-polymerization reaction, using a vapor deposition-polymerization device as shown in FIG. 1. The heat exchanger 5 was arranged in the device such that the heat-radiating plates 5*a* thereof faced the front of the device. This heat exchanger 5 was suspended from the ceiling 1*a* of the vapor deposition-polymerization device 1 by a cable 6, which could sufficiently withstand a desired tension in such a manner that all of the faces of the heat exchanger to be subjected to an anti-bacterial treatment were exposed or were not covered.

Using the vapor deposition-polymerization device 1, the device 1 was first evacuated through the exhaust valve communicated to the vacuum exhaust port 4, while a heat exchanger 5 was positioned within the device 1, to thus establish, within the device 1, a reduced pressure of $10^{-2}$ Pa. Then the temperature in the device was adjusted to 200° C. by the temperature control means while maintaining the foregoing pressure and such conditions were maintained. At this stage, gaseous 3,5-diamino-benzoic acid (DBA) contained in a container heated to 200° C. in advance was introduced into the device through the first gas inlet 2 and, simultaneously, gaseous pyromellitic acid dianhydride (PMDA) contained in a container likewise previously heated to 190.5° C. was introduced into the device through the second gas inlet 3. Then the vapor deposition-polymerization reaction on the surface of the heat exchanger 5 was continued over one hour under these conditions. After the completion of the vapor deposition-polymerization reaction, it was found that the entire surface of the heat exchanger 5 was uniformly covered with an anti-bacterial polymer film having a thickness of 1 µm. Regarding the thermal properties of the resulting anti-bacterial polymer film, the film had a high thermal decomposition-initiation temperature on the order of 530° C. and thus it was confirmed that the film was quite excellent in the heat resistance.

Separately, the same procedures used above were repeated except that oxydianiline (ODA) was substituted for the diaminobenzoic acid (DBA) to thus cover the surface of a heat exchanger with a conventional polyimide film, for the investigation of the anti-bacterial effect of the anti-bacterial polyimide film of the present invention while comparing the same with the heat exchanger covered with the conventional polyimide film and a heat exchanger free of any film. The test for anti-bacterial effects was carried out using *Staphylococcus aureus* and *Escherichia coli* according to the test method specified in JIS Z-2801. The results thus obtained are summarized in the following Table 1.

TABLE 1

Results of Test for Anti-bacterial Effect

| Sample | Viable Cell Count | Antibacterial Activity Value |
|---|---|---|
| (A) *Staphylococcus aureus* | | |
| Specimen covered with the anti-bacterial polyimide film according to the present invention | ≦10 | ≧3.4 |
| Specimen covered with the conventional polyimide film | $1.9 \times 10^6$ | −1.8 |
| Specimen free of any anti-bacterial film (immediately after the inoculation) | $3.5 \times 10^5$ | — |
| Specimen free of any anti-bacterial film (after 24 hrs.) | $2.7 \times 10^4$ | — |
| (B) *Escherichia coli* | | |
| Specimen covered with the anti-bacterial polyimide film according to the present invention | $2.0 \times 10^5$ | 2.0 |
| Specimen covered with the conventional polyimide film | $1.6 \times 10^7$ | 0.1 |
| Specimen free of any anti-bacterial film (immediately after the inoculation) | $3.8 \times 10^6$ | — |
| Specimen free of any anti-bacterial film (after 24 hrs.) | $2.0 \times 10^7$ | — |

As will be seen from the data listed in Table 1, the anti-bacterial polyimide film according to the present invention clearly shows an excellent anti-bacterial activity against *Staphylococcus aureus* and *Escherichia coli*.

EXAMPLE 2

The same procedures for the vapor deposition-polymerization reaction used in Example 1 were repeated except that 2,3-diaminobenzoic acid, 2,4-diaminobenzoic acid, 2,5-diaminobenzoic acid or 3,4-diaminobenzoic acid was substituted for the DBA used in Example 1 as one of the components used for forming an anti-bacterial polymer film or the diaminobenzoic acid monomer to be introduced into the device through the first gas-introduction port 2 to thus give a polymer film corresponding to each diaminobenzoic acid monomer. The resulting films were likewise inspected for the anti-bacterial effect according to the same anti-bacterial test used in Example 1 and as a result, it was found that each film showed good anti-bacterial properties.

EXAMPLE 3

The same procedures for the vapor deposition-polymerization reaction used in Example 1 were repeated except that 4,4'-methylenebis(2-chlorobenzene amine), 3,3'-dichloro-4,4'-diaminodiphenyl ether or 5-chloro-m-phenylenediamine was substituted for the DBA used in Example 1 as a monomer to be introduced into the device through the first gas-introduction port 2 to thus give a polymer film corresponding to each of the monomers. The resulting films were likewise inspected for the anti-bacterial effect according to the same anti-bacterial test used in Example 1 and as a result, it was found that each film showed good anti-bacterial properties.

EXAMPLE 4

The same procedures for the vapor deposition-polymerization reaction used in Example 1 were repeated except that oxy-diphthalic acid dianhydride as an acid dianhydride, 4,4'-methylene-bis(phenyl isocyanate) as a diisocyanate, terephthaloyl dichloride as an acid chloride or terephthal aldehyde as an aldehyde was used as the other component for forming an anti-bacterial polymer film or the monomer to be introduced into the device through the second gas-introduction port 3 to thus give a polymer film corresponding to each monomer. The resulting films were likewise inspected for the anti-bacterial effect according to the same anti-bacterial test used in Example 1 and as a result, it was found that each film showed good anti-bacterial properties.

As has been discussed above in detail, the present invention permits the preparation of a useful and excellent anti-bacterial polymer through the vapor deposition-polymerization reaction of a diaminobenzoic acid monomer or halogen atom-containing diamine monomer and a monomer reactive with the diaminobenzoic acid monomer or halogen atom-containing diamine monomer. Moreover the method for preparing a film consisting of such an anti-bacterial polymer comprises a vapor deposition-polymerization reaction and therefore, the method permits the formation of a film having a desired thickness even on the surface having a complicated shape such as the surface of, for instance, a heat exchanger.

What is claimed is:

1. An anti-bacterial polymer consisting of the vapor deposition-polymerization reaction product of a diaminobenzoic acid monomer and a monomer reactive with the diaminobenzoic acid monomer.

2. The anti-bacterial polymer as set forth in claim 1, wherein the diaminobenzoic acid monomer is a member selected from the group consisting of 2,3-diaminobenzoic acid, 2,4-diaminobenzoic acid, 2,5-diaminobenzoic acid, 3,4-diaminobenzoic acid and 3,5-diaminobenzoic acid.

3. The anti-bacterial polymer as set forth in claim 1, wherein the monomer reactive with the diaminobenzoic acid monomer is a member selected from the group consisting of tetracarboxylic acid dianhydrides, diisocyanates, acid chlorides and aldehydes.

4. An anti-bacterial polymer film consisting of an anti-bacterial polymer as set forth in claim 3.

5. An article characterized in that it comprises, on the surface thereof, an anti-bacterial polymer film comprising an anti-bacterial polymer asset forth in claim 3.

6. The anti-bacterial polymer as set forth in claim 1, wherein the anti-bacterial polymer is a polyimide, a polyamide, a polyurea or a poly(azomethine), the polyimide is a copolymer comprising at least one structural unit represented by the following formula (I):
(in the formula (I), Ar and

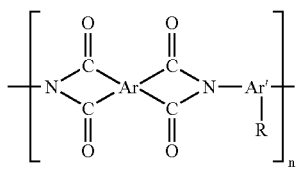

Ar' each represents an aromatic or aliphatic group, and R is COOH); the polyamide is a copolymer comprising at least one structural unit represented by the following formula (II):

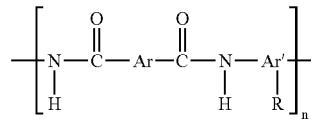

(in the formula (II), Ar and Ar' each represents an aromatic or aliphatic group, and R is COOH); the polyurea is a copolymer comprising at least one structural unit represented by the following formula (III):

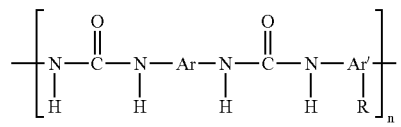

(in the formula (III), Ar and Ar' each represents an aromatic or aliphatic group, and R is COOH); and the poly(azomethine) is a copolymer comprising at least structural unit represented by the following formula (IV):

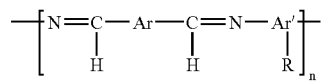

(in the formula (IV), Ar and Ar' each represents an aromatic or aliphatic group, and R is COOH).

7. An anti-bacterial polymer film consisting of an anti-bacterial polymer as set forth in claim 1, 2 or 6.

8. An article characterized in that it comprises, on the surface thereof, an anti-bacterial polymer film comprising an anti-bacterial polymer as set forth in claim 1, 2 or 6.

9. A method for the preparation of an anti-bacterial polymer comprising the step of subjecting a gas obtained by evaporating a diaminobenzoic acid monomer and a gas obtained by evaporating a monomer reactive with the diaminobenzoic acid monomer to vapor deposition-polymerization, in a vacuum, to thus form an anti-bacterial polymer.

10. The method for preparing an anti-bacterial polymer as set forth in claim 9, wherein the diaminobenzoic acid monomer is a member selected from the group consisting of 2,3-diaminobenzoic acid, 2,4-diaminobenzoic acid, 2,5-di-amino-benzoic acid, 3,4-diaminobenzoic acid and 3,5-di-aminobenzoic acid; and the monomer reactive with the diaminobenzoic acid monomer is a member selected from the group consisting of tetracarboxylic acid dianhydrides, diisocyanates, acid chlorides and aldehydes; and the anti-bacterial polymer is a polyimide, a polyamide, a polyurea or a poly(azomethine).

11. The method for preparing an anti-bacterial polymer as set forth in claim 10, wherein the polyimide is a copolymer comprising at least one structural unit represented by the following formula (I):

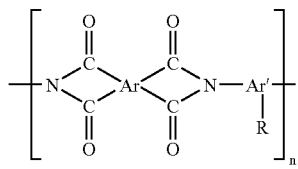

(in the formula (I), Ar and Ar' each represents an aromatic or aliphatic group, and R is COOH); the polyamide is a copolymer comprising at least one structural unit represented by the following formula (II):

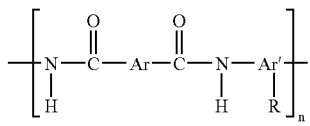

(in the formula (II), Ar and Ar' each represents an aromatic or aliphatic group, and R is COOH); the polyurea is a copolymer comprising at least one structural unit represented by the following formula (III):

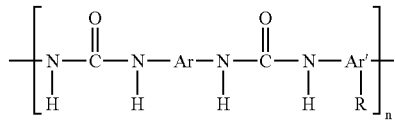

(in the formula (III), Ar and Ar' each represents an aromatic or aliphatic group, and R is COOH); and the poly(azomethine) is a copolymer comprising at least one structural unit represented by the following formula (IV):

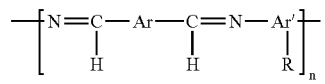

(in the formula (IV), Ar and Ar' each represents an aromatic or aliphatic group, and R is COOH).

12. A method for preparing an anti-bacterial polymer film comprising the step of subjecting a gas obtained by evaporating a diaminobenzoic acid -monomer and a gas obtained by evaporating a monomer reactive with the diaminobenzoic acid monomer to vapor deposition-polymerization on a substrate, in a vacuum, to thus form an anti-bacterial polymer.

13. The method for preparing an anti-bacterial polymer film as set forth in claim 12, wherein the diaminobenzoic acid monomer is a member selected from the group consisting of 2,3-diaminobenzoic acid, 2,4-diamino-benzoic acid, 2,5-diaminobenzoic acid, 3,4-diaminobenzoic acid and 3,5-diaminobenzoic acid; the monomer reactive with the diaminobenzoic acid monomer is a member selected from the group consisting of tetracarboxylic acid dianhydrides, diisocyanates, acid chlorides and aldehydes; and the anti-bacterial polymer is a polyimide, a polyamide, a polyurea or a poly(azomethine).

* * * * *